(12) United States Patent
Braun et al.

(10) Patent No.: US 7,285,121 B2
(45) Date of Patent: Oct. 23, 2007

(54) DEVICES AND METHODS FOR THE CORRECTION AND TREATMENT OF SPINAL DEFORMITIES

(75) Inventors: John T. Braun, Salt Lake City, UT (US); Fred J. Molz, Collierville, TN (US); Troy D. Drewry, Memphis, TN (US); Michael C. Sherman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 872 days.

(21) Appl. No.: 10/137,039

(22) Filed: May 2, 2002

(65) Prior Publication Data

US 2003/0088251 A1    May 8, 2003

Related U.S. Application Data

(60) Provisional application No. 60/337,937, filed on Nov. 5, 2001.

(51) Int. Cl.
  *A61B 17/58* (2006.01)
  *A61B 17/70* (2006.01)

(52) U.S. Cl. ............................ 606/73; 606/61; 606/72; 606/60

(58) Field of Classification Search .................. 606/61, 606/72, 60, 73, 62, 69, 100, 96, 101; 623/16.11, 623/17.11
See application file for complete search history.

(56) References Cited

U.S. PATENT DOCUMENTS

| | | |
|---|---|---|
| 16,151 A | 12/1856 | Stone et al. |
| 376,427 A | 1/1888 | Cassidy |
| 817,042 A | 4/1906 | Burns |
| 1,079,630 A | 11/1913 | Baum |
| 1,409,825 A | 3/1922 | Brush |
| 2,112,007 A | 3/1938 | Adams |
| 2,347,567 A | 4/1944 | Kresse |
| 2,387,720 A | 10/1945 | Davis |
| 3,067,740 A | 12/1962 | Haboush |
| 3,298,372 A | 1/1967 | Feinberg |
| 3,426,364 A | 2/1969 | Lumb |
| 3,499,222 A | 3/1970 | Linkow et al. |
| 3,579,831 A | 5/1971 | Stevens et al. |
| 3,589,011 A | 6/1971 | Sneer |
| 3,732,621 A | 5/1973 | Bostrom |
| 3,848,601 A | 11/1974 | Ma et al. |
| 3,867,728 A | 2/1975 | Stubstad et al. |
| 3,875,595 A | 4/1975 | Froning |
| 3,997,138 A | 12/1976 | Crock et al. |
| 4,011,602 A | 3/1977 | Rybicki et al. |
| 4,016,651 A | 4/1977 | Kawahara et al. |
| 4,041,939 A | 8/1977 | Hall |

(Continued)

FOREIGN PATENT DOCUMENTS

DE    27 26 297 A1    12/1978

(Continued)

*Primary Examiner*—Cris Rodriguez
*Assistant Examiner*—Candice C. Stokes
(74) *Attorney, Agent, or Firm*—Krieg DeVault LLP

(57) ABSTRACT

One or more anchors are engaged intravertebrally for attachment of one more constructs thereto to correct or treat spinal conditions or deformities. Methods for inserting the anchors are also provided along with constructs for attachment to the anchors.

61 Claims, 13 Drawing Sheets

U.S. PATENT DOCUMENTS

| | | |
|---|---|---|
| 4,044,508 A | 8/1977 | Frederick |
| 4,140,432 A | 2/1979 | Heule |
| 4,162,867 A | 7/1979 | Calcaterra et al. |
| 4,259,072 A | 3/1981 | Hirabayashi et al. |
| 4,309,777 A | 1/1982 | Patil |
| 4,328,593 A | 5/1982 | Sutter et al. |
| 4,332,036 A | 6/1982 | Sutter et al. |
| 4,349,921 A | 9/1982 | Kuntz |
| 4,369,769 A | 1/1983 | Edwards |
| 4,401,112 A | 8/1983 | Rezaian |
| 4,463,753 A | 8/1984 | Gustilo |
| 4,468,200 A | 8/1984 | Munch |
| 4,479,491 A | 10/1984 | Martin |
| 4,484,570 A | 11/1984 | Sutter et al. |
| 4,486,178 A | 12/1984 | Schulte |
| 4,501,269 A | 2/1985 | Bagby |
| RE31,865 E | 4/1985 | Roux |
| 4,547,157 A | 10/1985 | Driskell |
| 4,552,532 A | 11/1985 | Mozsary |
| 4,553,273 A | 11/1985 | Wu |
| 4,554,914 A | 11/1985 | Kapp et al. |
| 4,573,448 A | 3/1986 | Kambin |
| 4,589,414 A | 5/1986 | Yoshida et al. |
| 4,599,086 A | 7/1986 | Doty |
| 4,603,694 A | 8/1986 | Wheeler |
| 4,612,922 A | 9/1986 | Barber |
| 4,626,214 A | 12/1986 | Artal |
| 4,636,217 A | 1/1987 | Ogilvie et al. |
| 4,644,951 A | 2/1987 | Bays |
| 4,646,738 A | 3/1987 | Trott |
| 4,653,481 A | 3/1987 | Howland et al. |
| 4,657,550 A | 4/1987 | Daher |
| 4,668,191 A | 5/1987 | Plischka |
| 4,686,997 A | 8/1987 | Oloff et al. |
| 4,690,595 A | 9/1987 | Heule |
| 4,696,292 A | 9/1987 | Heiple |
| 4,712,681 A | 12/1987 | Branemark et al. |
| 4,713,004 A | 12/1987 | Linkow et al. |
| 4,714,469 A | 12/1987 | Kenna |
| 4,714,478 A | 12/1987 | Fischer |
| 4,743,256 A | 5/1988 | Brantigan |
| 4,743,260 A | 5/1988 | Burton |
| 4,756,649 A | 7/1988 | Heule |
| 4,769,041 A | 9/1988 | Morscher |
| 4,772,287 A | 9/1988 | Ray et al. |
| 4,782,833 A | 11/1988 | Einhorn et al. |
| 4,834,757 A | 5/1989 | Brantigan |
| 4,840,633 A | 6/1989 | Kallabis et al. |
| 4,842,518 A | 6/1989 | Linkow et al. |
| 4,870,957 A | 10/1989 | Goble et al. |
| 4,878,915 A | 11/1989 | Brantigan |
| 4,932,868 A | 6/1990 | Linkow et al. |
| 4,936,848 A | 6/1990 | Bagby |
| 4,936,851 A | 6/1990 | Fox et al. |
| 4,961,740 A | 10/1990 | Ray et al. |
| 5,011,484 A | 4/1991 | Breard |
| 5,015,247 A | 5/1991 | Michelson |
| 5,026,373 A | 6/1991 | Ray et al. |
| 5,055,104 A | 10/1991 | Ray |
| 5,092,866 A | 3/1992 | Breard et al. |
| 5,180,393 A | 1/1993 | Commarmond |
| 5,282,863 A | 2/1994 | Burton |
| 5,360,448 A | 11/1994 | Thramann |
| 5,387,213 A | 2/1995 | Breard et al. |
| 5,405,388 A | 4/1995 | Fox |
| 5,425,767 A | 6/1995 | Steininger et al. |
| 5,458,638 A | 10/1995 | Kuslich et al. |
| 5,489,307 A | 2/1996 | Kuslich et al. |
| 5,489,308 A | 2/1996 | Kuslich et al. |
| 5,496,318 A | 3/1996 | Howland et al. |
| 5,591,235 A | 1/1997 | Kuslich |
| 5,609,634 A | 3/1997 | Voydeville |
| 5,611,801 A * | 3/1997 | Songer ..................... 606/73 |
| 5,658,285 A | 8/1997 | Marney et al. |
| 5,669,909 A * | 9/1997 | Zdeblick et al. .............. 606/61 |
| 5,676,666 A | 10/1997 | Oxland et al. |
| 5,702,397 A * | 12/1997 | Goble et al. .................. 606/72 |
| 5,702,445 A | 12/1997 | Branemark |
| 5,707,395 A | 1/1998 | Li |
| 5,725,582 A | 3/1998 | Bevan et al. |
| RE35,784 E | 5/1998 | Linkow et al. |
| 5,895,427 A | 4/1999 | Kuslich et al. |
| 5,904,704 A | 5/1999 | Goble et al. |
| 5,906,616 A | 5/1999 | Pavlov et al. |
| RE36,221 E | 6/1999 | Breard et al. |
| 5,951,560 A * | 9/1999 | Simon et al. ................. 606/73 |
| 6,015,937 A | 1/2000 | Branemark |
| 6,019,760 A | 2/2000 | Metz-Stavenhagen |
| 6,053,916 A | 4/2000 | Moore |
| 6,056,749 A | 5/2000 | Kuslich |
| 6,139,551 A | 10/2000 | Michelson et al. |
| 6,149,650 A | 11/2000 | Michelson |
| 6,149,686 A | 11/2000 | Kuslich et al. |
| 6,190,388 B1 | 2/2001 | Michelson et al. |
| RE37,161 E | 5/2001 | Michelson et al. |
| 6,235,028 B1 | 5/2001 | Brumfield et al. |
| 6,287,343 B1 | 9/2001 | Kuslich et al. |
| 6,296,643 B1 | 10/2001 | Hopf et al. |
| 6,299,613 B1 | 10/2001 | Ogilvie et al. |
| RE37,479 E | 12/2001 | Kuslich |
| 6,436,099 B1 | 8/2002 | Drewry et al. |
| 6,565,573 B1 * | 5/2003 | Ferrante et al. ................ 606/73 |
| 6,610,080 B2 * | 8/2003 | Morgan ..................... 606/232 |
| 6,616,669 B2 | 9/2003 | Ogilvie et al. |
| 6,743,233 B1 * | 6/2004 | Baldwin et al. .............. 606/73 |
| 6,783,527 B2 | 8/2004 | Drewry et al. |
| 2002/0082598 A1 * | 6/2002 | Teitelbaum ................... 606/61 |
| 2002/0120270 A1 | 8/2002 | Trieu et al. |
| 2003/0023241 A1 | 1/2003 | Drewry et al. |
| 2004/0138666 A1 | 7/2004 | Molz et al. |
| 2004/0172025 A1 | 9/2004 | Drewry et al. |
| 2005/0171539 A1 | 8/2005 | Braun et al. |
| 2005/0192581 A1 | 9/2005 | Molz et al. |
| 2005/0216004 A1 | 9/2005 | Schwab |

FOREIGN PATENT DOCUMENTS

| | | |
|---|---|---|
| DE | 30 43 336 A1 | 6/1981 |
| DE | 30 27 138 A1 | 12/1981 |
| DE | 32 41 963 C1 | 4/1984 |
| DE | 43 02 397 A1 | 7/1993 |
| EP | 0 139 052 A1 | 5/1985 |
| EP | 0 307 241 B1 | 3/1989 |
| FR | 2.085.013 | 12/1971 |
| FR | 2 710 519 A1 | 4/1995 |
| GB | 1 291 470 | 10/1972 |
| GB | 1 352 188 | 5/1974 |
| GB | 1 565 178 | 4/1980 |
| GB | 2 119 258 A | 11/1983 |
| WO | WO88/06023 | 8/1988 |

* cited by examiner

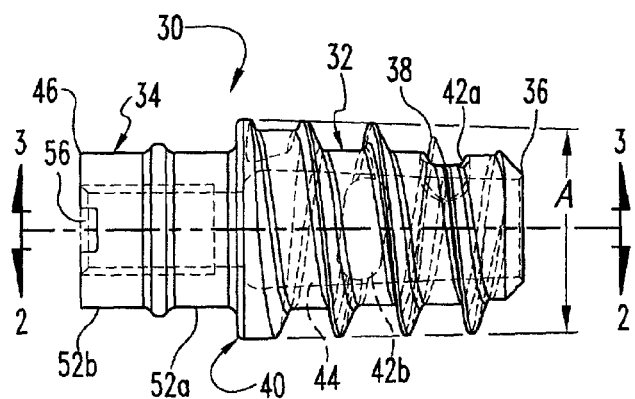
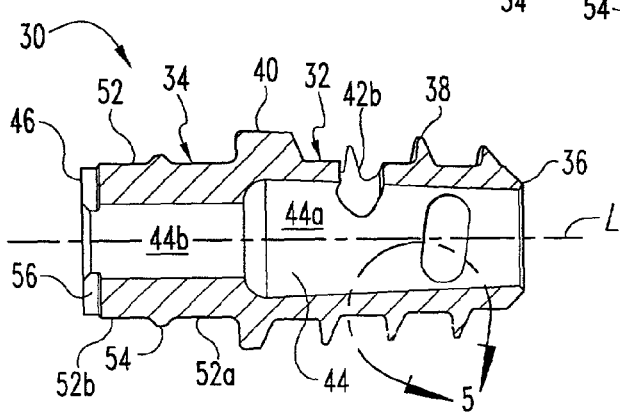
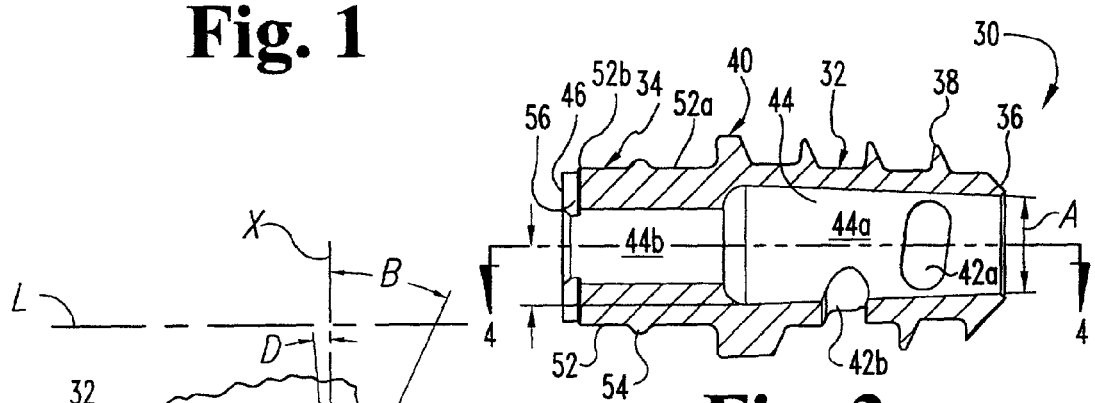
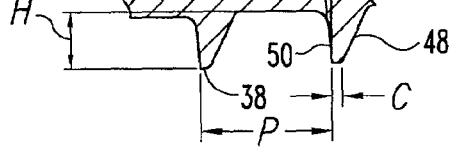
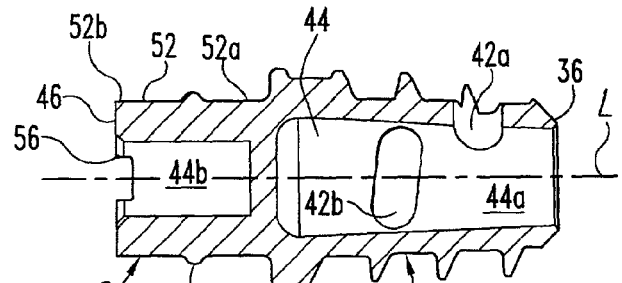

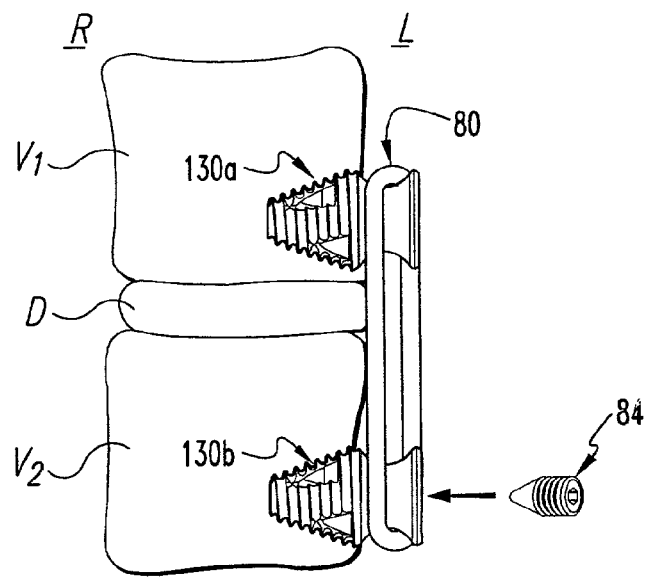
Fig. 19
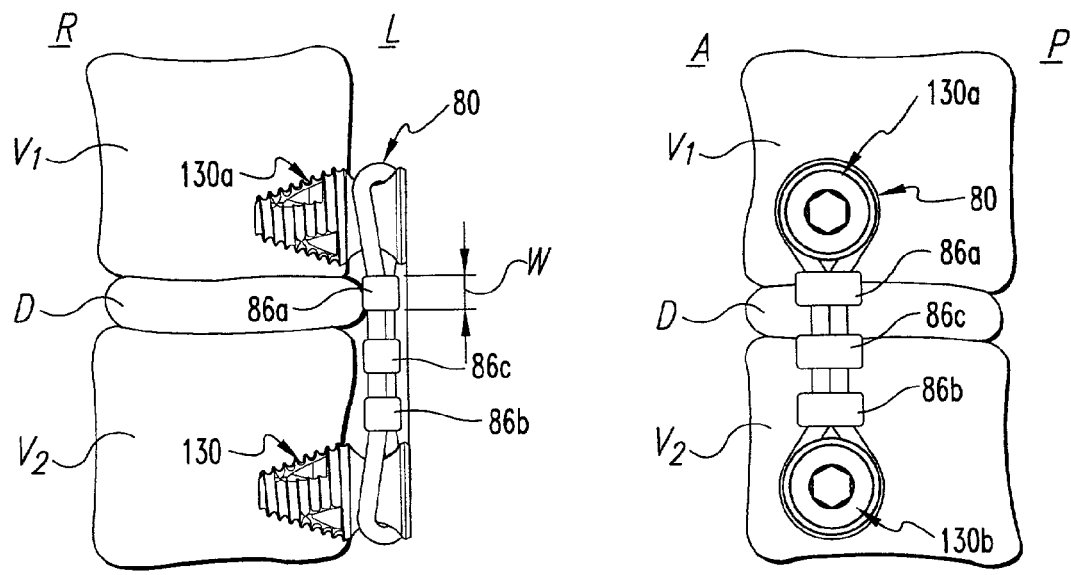
Fig. 20a  Fig. 20b

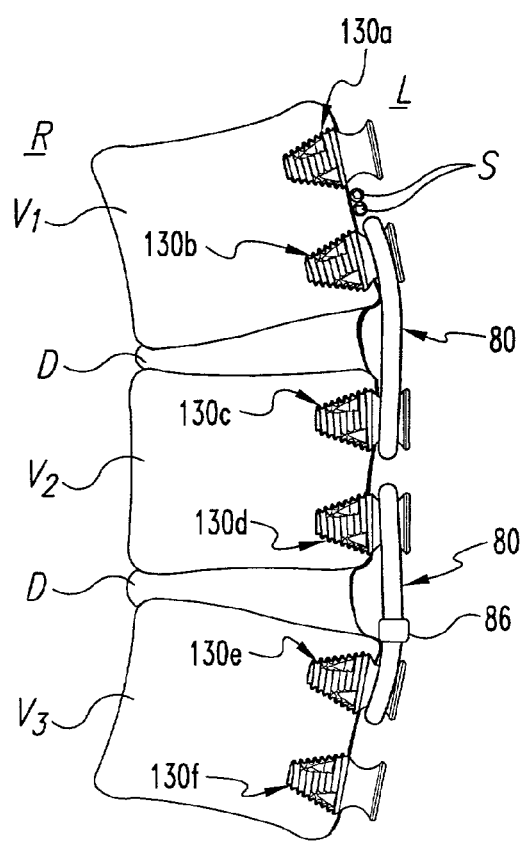
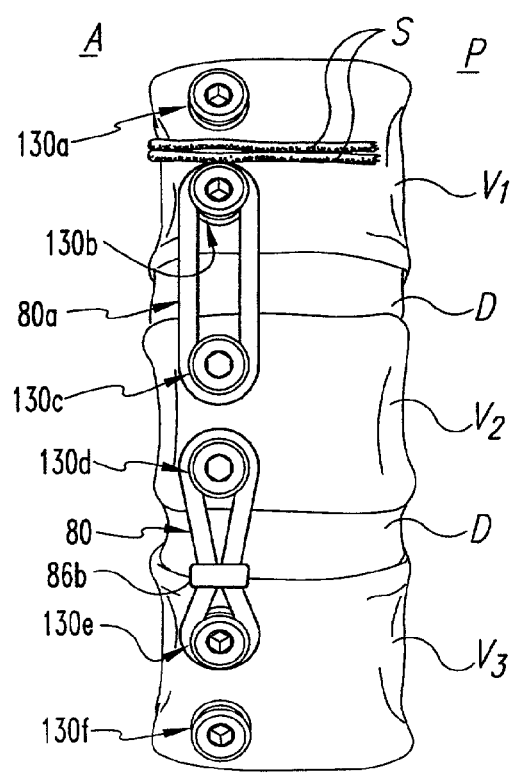
Fig. 21a  Fig. 21b

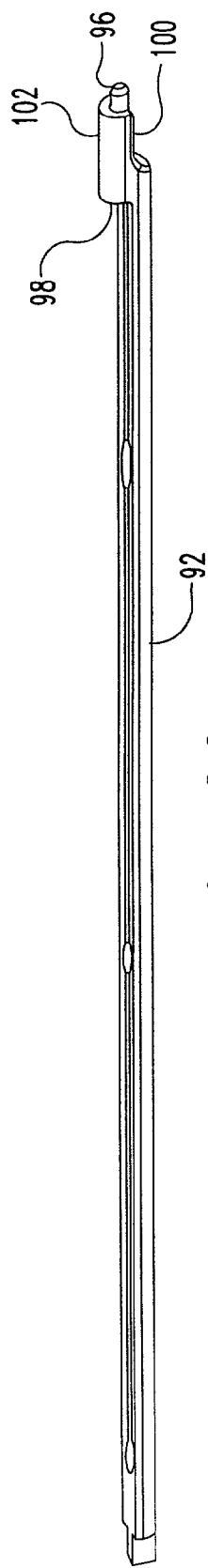
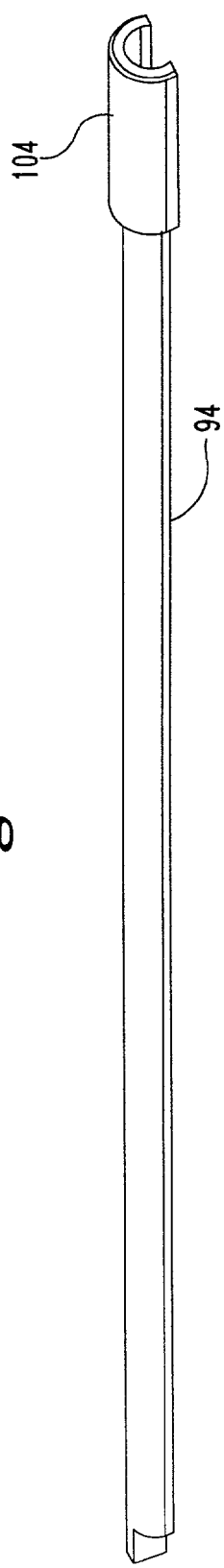
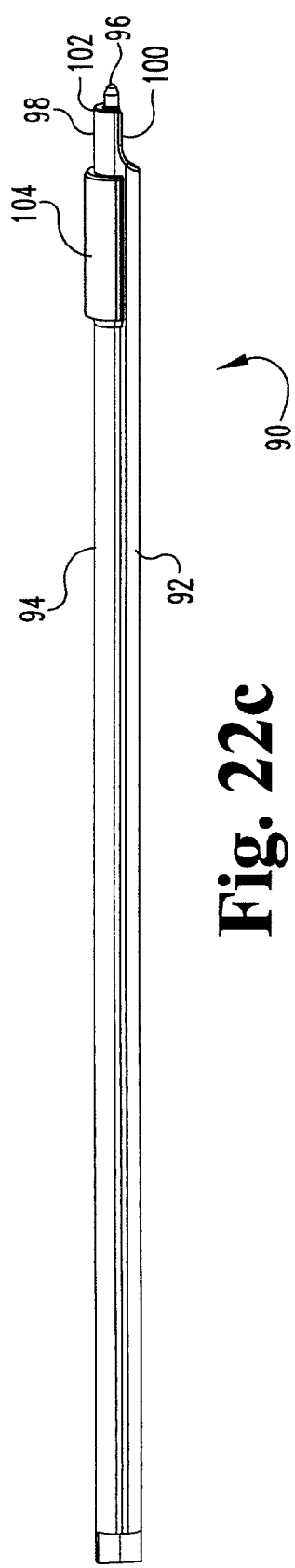
Fig. 22a
Fig. 22b
Fig. 22c

DEVICES AND METHODS FOR THE CORRECTION AND TREATMENT OF SPINAL DEFORMITIES

CROSS-REFERENCE TO RELATED APPLICATION

The present application claims the benefit of the filing date of Provisional Application No. 60/337,937 filed on Nov. 5, 2001.

BACKGROUND OF THE INVENTION

Several systems and devices are available from various manufacturers to provide correction and stabilization of the spine. Such systems and devices can include screws engaged to the vertebral bodies and configured for engagement with elongated rods or plates that extend along the vertebral bodies. Device for fusing adjacent vertebrae and artificial disc replacement are also available. Furthermore, nonoperative devices and methods, such as bracing and observation, can be used whenever applicable.

Although these prior systems and devices exist, there remains a need for improved devices, systems and methods for treating spinal deformities and other conditions of the spine. There also remains a need for improved devices for connecting implants, plates, elongate members and other devices to one or more vertebral bodies. The present invention satisfies these needs, among others, in a novel and non-obvious way.

BRIEF DESCRIPTION OF THE DRAWINGS

FIG. 1 is an elevational view of a bone anchor according to one embodiment of the present invention.

FIG. 2 is a section view through line 2-2 of FIG. 1.

FIG. 3 is a section view through line 3-3 of FIG. 1.

FIG. 4 is a section view through line 4-4 of FIG. 3.

FIG. 5 is an enlarged detail view of a portion of the bone anchor at the location indicated in FIG. 2.

FIG. 19 is an anterior view illustrating the attachment of a plug to one of the bone anchors after engagement of the tether to the bone anchors.

FIGS. 20a and 20b are anterior and lateral views, respectively, showing the crimping of the tether engaged to the bone anchors.

FIGS. 21a and 21b are anterior and lateral views, respectively, showing an embodiment of a system of interconnecting three vertebral bodies with the bones anchors and tethers.

FIGS. 22a, 22b and 22c are perspective views of an inner shaft, an outer shaft, and the assembly of the inner and outer shafts, respectively, of a tether loading instrument.

DESCRIPTION OF THE ILLUSTRATED EMBODIMENTS

Figure 6:
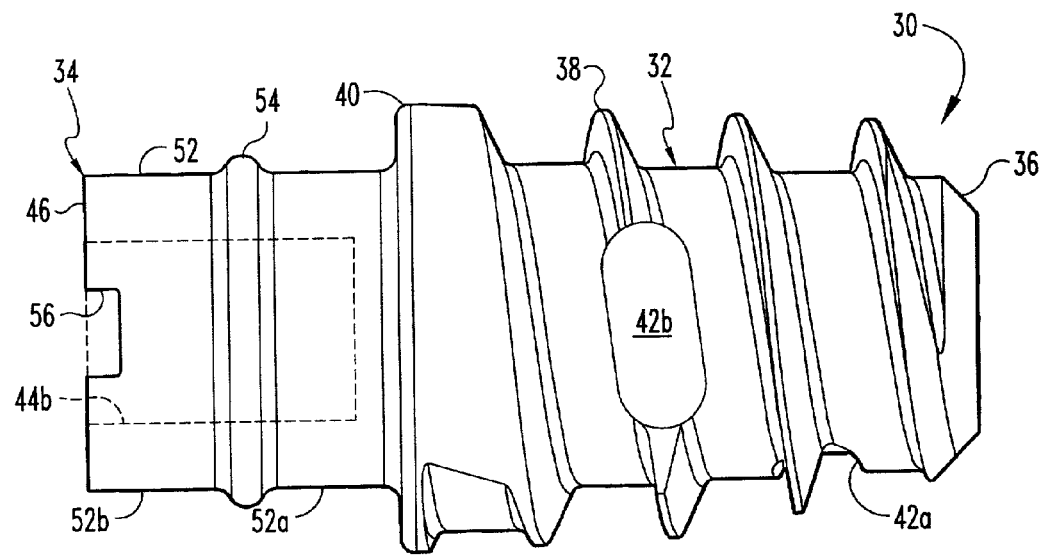
FIG. 6 is an enlarged elevational view of the bone anchor of FIG. 1 rotated 180 degrees about its central axis.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein are contemplated as would normally occur to one skilled in the art to which the invention relates.

The present invention provides anchors engageable intravertebrally to bony tissue of a vertebral body. The anchors provide solid bony attachment to the vertebra within a spinal column segment rather than between motion segments. The anchors have application in, for example, the correction of spinal deformities, the temporary or permanent rigid fixation of bone, the temporary or permanent flexible fixation of bone, as a buttress for bone grafting techniques for the spine, and for fusionless scoliosis surgery.

The anchors have a first portion embedded into the vertebral body that can be configured to engage undisturbed bone so that the anchor is well secured to the vertebral body. The anchor can be tapered and provided with a frusto-conical shape along the length of the embedded portion such that the size of the distal insertion end of the embedded portion is less than the size of the proximal end of the embedded portion. The frusto-conical shape of the anchors provides a greater margin of safety for the surgeon inserting anchor. The smaller distal end reduces the chance for the anchor to penetrate a vertebral endplate should the anchor be inserted into the vertebral body at an angle toward the endplate. The frusto-conical shape of the embedded portion also provides a large surface area in contact with undisturbed bone and also a large surface area over which to distribute the anchor loads. Loading on the anchor head is more evenly distributed over the embedded portion of the anchor since the larger end of the frusto-conical portion is located adjacent the head of the anchor where the anchor load is applied.

The anchors can include an inner chamber and at least one opening in communication with the chamber to allow fusion of the anchor with the vertebral body. The embedded portion of the anchor can further be provided with bone cutting threads and openings through which the cut bone is harvested and deposited into the chamber of the anchor. The chamber can extend throughout the length of the anchor to encourage undisturbed bone to enter the chamber upon initial placement into the vertebral body and to remain in continuity with the host bone. The chamber can also be packed with graft material alone or in combination with harvested bone. A cap or plug can be engaged to the anchor to compress the harvested bone and/or graft material in the chamber of the anchor.

The anchors described herein can be made from any biocompatible material, including synthetic or natural autograft, allograft or xenograft tissues, and can be resorbable or non-resorbable nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are carbon-reinforced polymer composites, shape-memory alloys, titanium, titanium alloys, cobalt chrome alloys, stainless steel, ceramics and combinations thereof.

Referring to FIGS. 1-5, one embodiment of an anchor will be further described. Anchor 30 includes a body 32 and a head 34 extending proximally from a proximal end 40 of body 32. Body 32 extends along a central longitudinal axis L distally from proximal end 40 to a distal insertion end 36. Insertion end 36 can be beveled to facilitate insertion of anchor 30 into bony tissue. A thread form 38 is formed along body 32 from distal end 36 to proximal end 40 where thread form 38 runs out. Body 32 has a frusto-conical configuration that tapers from a maximum size at proximal end 40 to a minimum size at distal end 36. Thread form 38 can be a continuous single thread, a series of threads, or other structure that engages bony tissue and facilitates advancement of body 32 into the vertebra, such as barbs.

In one specific embodiment, this taper forms an angle A of about 5 degrees. In a further specific embodiment, it is contemplated that body 32 can be provided with a length along axis L of between about 5 to 25 millimeters and a maximum diameter at proximal end 40 of about 10 to 20 millimeters. Other embodiments contemplate lengths and diameters outside these ranges.

Body 32 further includes a number of openings 42 formed therethrough and in communication with a chamber 44. Chamber 44 extends through anchor 30 and opens at the proximal end 46 of head 34 and also opens at the distal end 36 of body 32. Chamber 44 is also tapered at angle A, although other shapes are also contemplated. Chamber 44 has a distal portion 44a in body 32 and a proximal portion 44b in head 34. Openings 42 interrupt thread form 38 and provide an avenue for deposit of bony tissue into chamber 44 as it is severed by thread form 38 during threaded insertion of anchor 30 into bony tissue. The tapered shape of body 32 allows thread form 38 to engage undisturbed bone as it is inserted, and also allows body 32 to be embedded into the vertebral body in engagement with undisturbed bone. This enhances the pullout resistance capability of thread form 38.

In the illustrated embodiment, two openings 42 are positioned about body 32 and located along thread form 38. The openings 42 are spaced along thread form 38 so that at least one complete revolution of body 32 is required for the proximal opening 42b to occupy the location previously occupied by the distal opening 42a. This allows the proximal opening 42b to pickup freshly cut bone from thread form 38 that was not cut by the smaller sized portion of body 32 located distally of the distal opening 42a and proximal opening 42b. Openings 42 are also staggered about the perimeter of body 32, thereby enhancing its structural integrity and load carrying capability.

The opening at distal end 36 provides continuity with the host bone. As body 32 is threaded into the vertebrae, cancellous bone enters into chamber 44 through the open distal end 36. This bone provides an in situ vascularized bone graft from the host bone in chamber 44. The bone harvested by thread form 38 and deposited through the openings 42 provides continuity between the in situ graft and the harvested bone. Since body 32 is engaged to undisturbed bony tissue, the harvested bone remains in continuity with the undisturbed host bone. These features enhance bone growth through body 32 and the fusion of anchor 30 to the vertebra.

Openings 42 are further provided with an oval shape that is centered on and extends along thread form 38 so that the bone severed by thread form 38 is deposited directly into the opening. Openings 42 are provided with a width transverse to thread form 38 sufficient to allow cut bone to be deposited therethrough into chamber 44 while minimizing the size of the openings in the wall of body 32. In one specific embodiment, the width of openings 42 is about 2 millimeters. Other widths along body 32 for openings 42 are also contemplated.

Thread form 38 has a configuration that minimizes overlap in successive thread turns in order to minimize the disturbance to the host bone as anchor 30 is inserted while providing sufficient penetration into and engagement with undisturbed bone to provide pull-out resistance. As shown in FIG. 5, axis X is perpendicular to central longitudinal axis L. Thread form 38 has a leading wall 48 sloped at an angle B with respect to axis X and a trailing wall slightly sloped at an angle D with respect to axis X. Thread form 38 has a thread crest dimension C, a pitch P along body 32, and a height H above the root diameter of body 32. In one specific embodiment, angle B is about 25 degrees, angle D is about 5 degrees, thread crest dimension C is about 0.17 millimeters, pitch P is about 3 millimeters, and height H is about 1.3 millimeters. It is also contemplated that other embodiments include other values for angle A, angle D, thread crest dimension C, pitch P and height H.

Head 34 extends from the vertebral body when body 32 is embedded therein. Head 34 can be provided with any configuration for attachment of a construct thereto for treatment or correction of a spinal condition or deformity. In the illustrated embodiment of FIGS. 1-5, head 34 has a member 52 extending proximally from proximal end 40 of body 32. Member 52 has a tool engaging recess 56 formed in its proximal end 46 for engagement with a driving tool, such as a screw driver, that can be used to threadingly insert body portion 32 into the vertebral body. Head 34 further includes a lip 54 extending around and outwardly from member 52 which separates member 52 into a distal platform 52a and a proximal platform 52b.

Figure 7:
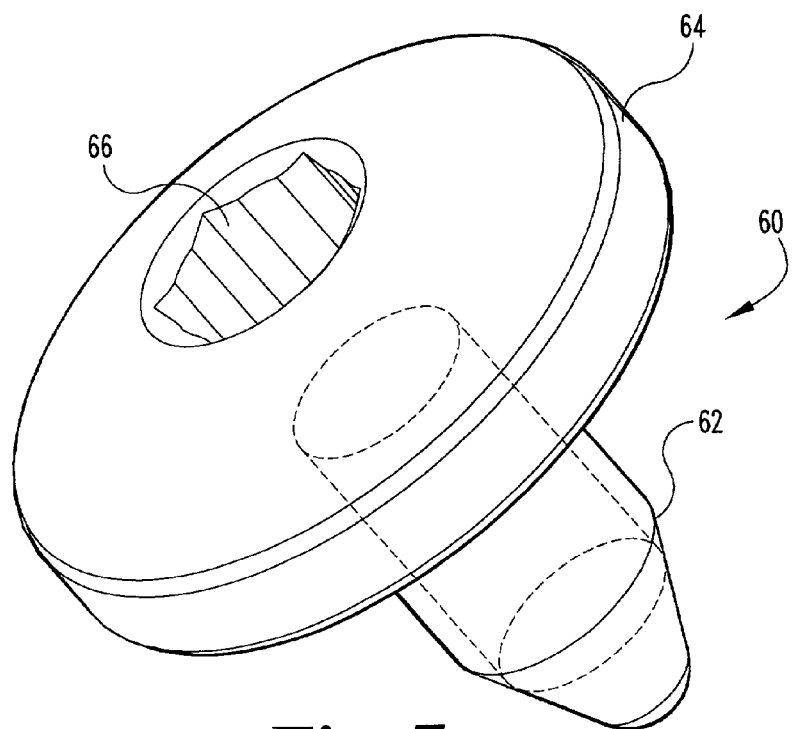
FIG. 7 is an enlarged perspective view of a cap engageable with the bone anchor of FIG. 6.
Figure 8:
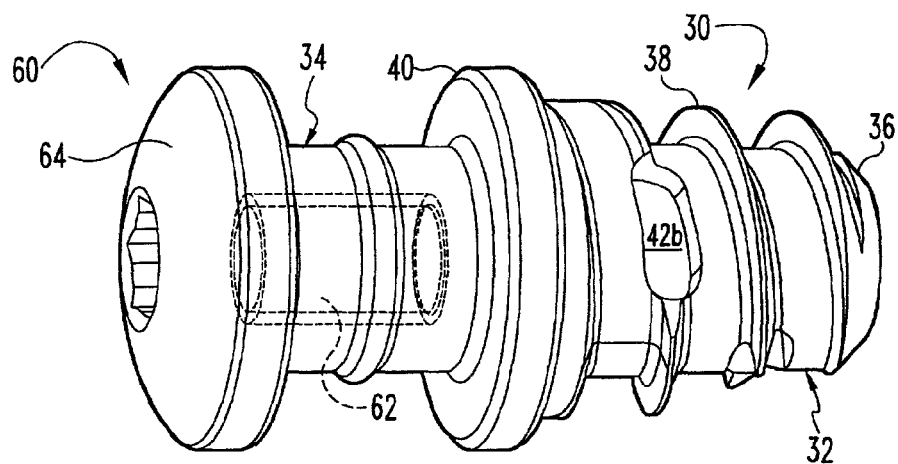
FIG. 8 is a perspective view showing the cap of FIG. 7 engaged to the bone anchor of FIG. 6.

Referring now to FIGS. 6 and 7, there is shown anchor 30 along with a cap 60 engageable to head 34 of anchor 30. Cap 60 has a stem 62 and an enlarged end member 64. End member 64 has a tool engaging opening 66 formed in a proximal face thereof configured to receive hex-shaped driving tool or the like. Stem 62 can be threaded to engage threads provided in proximal portion 44b of chamber 44, as shown in FIG. 8. In the illustrated embodiment, end member 64 is larger than head 34 and extends radially therearound when cap 60 is engaged to anchor 30. Other embodiments contemplate that end member 64 is not larger than the head of the anchor. It is also contemplate that means other than threads, such as, for example, a friction or interference fit, a bayonet fit, or a snap fit, are provided to maintain cap 60 on head 34.

Stem 62 extends distally from end member 64, and can be provided with a length sufficient to compress harvested bone material and graft material placed in distal portion 44a of chamber 44 when cap 60 is engaged to anchor 30. The length and diameter of stem 62 can be varied between different caps 60 to provide the surgeon the ability to select a stem size that provides the desired amount of compression of graft and bone tissue in chamber 44. Compression of the harvested bone and graft material places maintains its contact with the host bone at the opening at distal end 36 and also at the openings 42 to promote fusion. Cap 60 further promotes fusion of anchor 30 to the host bone by preventing escape of the bony material from chamber 44.

Figure 9:
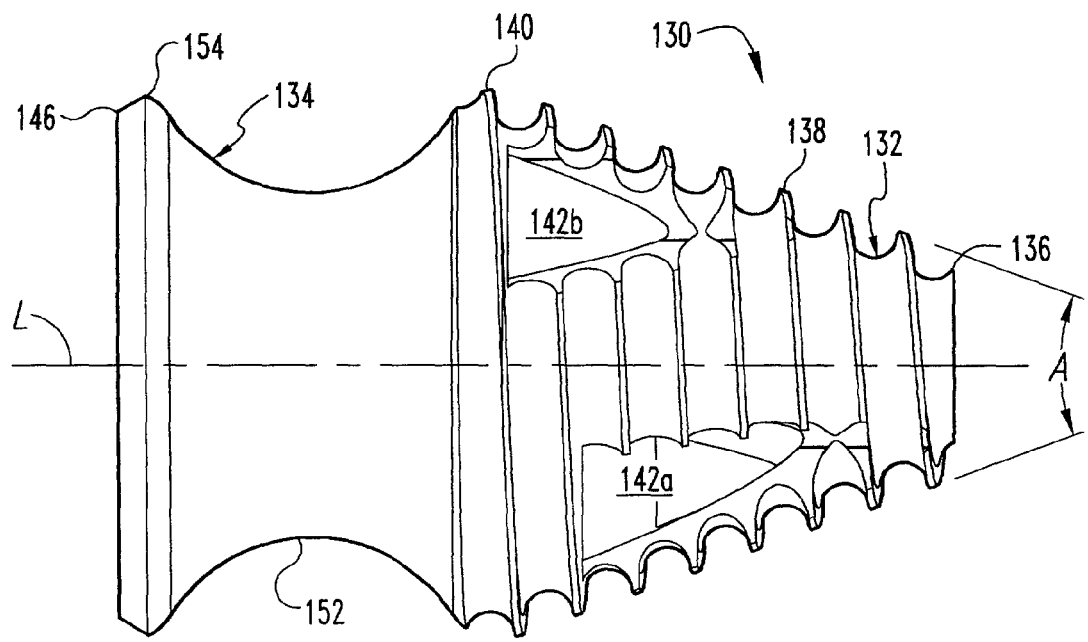
FIG. 9 is an elevational view of another embodiment bone anchor of the present invention.

In FIGS. 9-12 there are provided further embodiments of intravertebral anchors which provide at least some or all of the benefits discussed above with respect to anchor 30. In FIG. 9 anchor 130 includes a body 132 and a head 134 extending proximally from a proximal end 140 of body 132. Body 132 extends along a central longitudinal axis L distally from proximal end 140 to a distal insertion end 136. A thread form 138 is formed along body 132 from distal end 136 to proximal end 140 where thread form 138 runs out. Body 132 has a frusto-conical configuration that tapers from a maximum size at proximal end 140 to a minimum size at distal end 136. In one specific embodiment, this taper forms an angle A of about 40 degrees.

Body 132 further includes a number of openings 142 formed therethrough and in communication with an internal chamber that extends through anchor 130 and opens at the proximal end 146 of head 134 and also opens at the distal end 136 of body 132. Openings 142 interrupt thread form 138 and provide an avenue for deposit of bony tissue into the internal chamber as it is severed by thread form 138 during threaded insertion of anchor 130 into bony tissue. The tapered shape of body 132 allows thread form 138 to at least partially engage undisturbed bone as it is inserted, and also allows body 132 to be embedded into the vertebral body in at least partial engagement with undisturbed bone. This enhances the pullout resistance capability of thread form 138.

In the illustrated embodiment, two openings 142a, 142b are positioned about body 132 and located along thread form 138. Openings 142a, 142b are staggered about the perimeter of body 132, thereby enhancing its structural integrity and load carrying capability. Openings 142a, 142b are further provided with a triangular shape extending along thread form 138 with the apex of the triangular opening oriented distally and the base oriented proximally. Openings 142a, 142b overlap one another along the length of body 132. The leading edge of each opening 142 can be undercut through the wall of body 132 so that the threads and outer surface of body 132 form a cutting edge that extends along each opening to provide aggressive bone cutting and collection through each opening.

Head 134 extends from the vertebral body when body 132 is embedded therein. As described further below, head 134 can be provided with any configuration for attachment of a construct thereto for treatment or correction of a spinal condition or deformity. In the illustrated embodiment of FIG. 9, head 134 has a member 152 extending proximally from proximal end 140 of body 132. Member 152 can be provided with a tool engaging recess in its proximal end 146 for engagement with a driving tool used to threadingly insert body portion 132 into the vertebral body. Member 152 has a concave arc shape between proximal end 140 of body 132 and a lip 154 extending around and outwardly from member 152, providing a smooth platform for connection of a construct to anchor 130. The platform having a smooth arc shape reduces frictional wear on the construct engaged thereto. A plug or cap, such as cap 60, can be secured to head 134. The plug, such as plug 84 (FIG. 19) can be provided without an enlarged head since lip 154 can maintain the construct on the platform of member 152.

Figure 10:
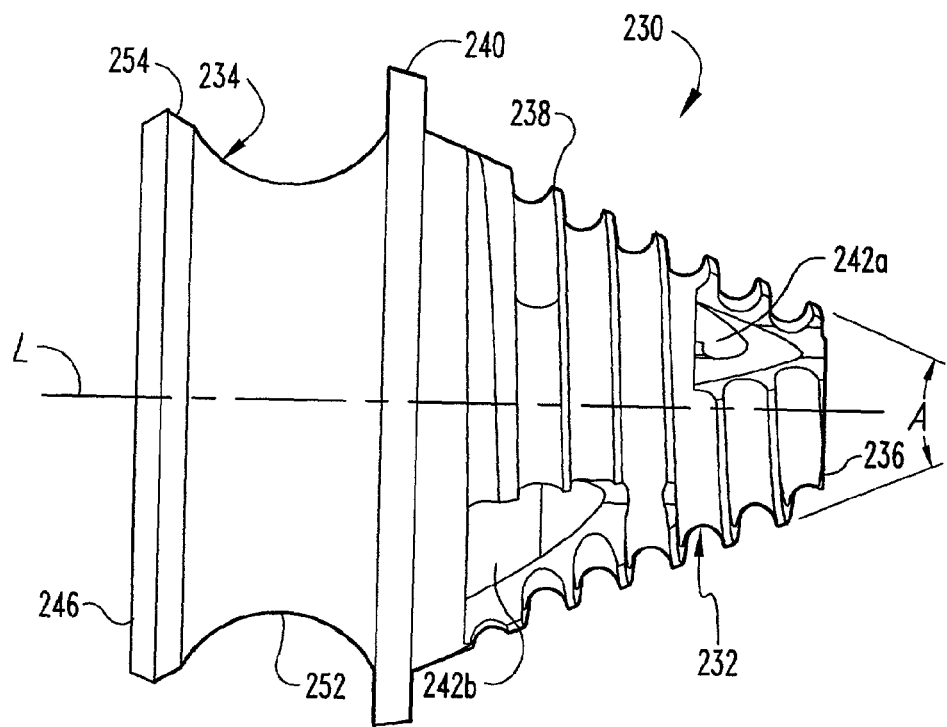
FIG. 10 is an elevational view of yet another embodiment bone anchor of the present invention.

In FIG. 10 anchor 230 includes a body 232 and a head 234 extending proximally from a proximal end 240 of body 232. Body 232 extends along a central longitudinal axis L distally from proximal end 240 to a distal insertion end 236. Proximal end 240 includes a ring shape extending radially about body 232, acting as an abutment or stop member against the vertebral body as anchor 230 is threaded therein. A thread form 238 is formed along body 232 from distal end 236 to proximal end 240 where thread form 238 runs out. Body 232 has a frusto-conical configuration that tapers from a maximum size at proximal end 240 to a minimum size at distal end 236. In one specific embodiment, this taper forms an angle A of about 45 degrees.

Body 232 further includes a number of openings 242 formed therethrough and in communication with an internal chamber that extends through anchor 230 and opens at the proximal end 246 of head 234 and also opens at the distal end 236 of body 232. Openings 242 interrupt thread form 238 and provide an avenue for deposit of bony tissue into the internal chamber as it is severed by thread form 238 during threaded insertion of anchor 230 into bony tissue. The tapered shape of body 232 allows thread form 238 to at least partially engage undisturbed bone as it is inserted, and also allows body 232 to be embedded into the vertebral body in at least partial engagement with undisturbed bone. This enhances the pullout resistance capability of thread form 238.

In the illustrated embodiment, two openings 242a, 242b are positioned about body 232 and located along thread form 238. Openings 242a, 242b are staggered about the perimeter of body 232, and are also staggered along the length of body 232 so that they do not overlap. Openings 242a, 242b are further provided with a triangular shape extending along thread form 238 with the apex of the triangular opening oriented distally and the base oriented proximally. The leading edge of the openings can be undercut to facilitate cutting and harvesting of bone.

Head 234 extends from the vertebral body when body 232 is embedded therein. As described further below, head 234 can be provided with any configuration for attachment of a construct thereto for treatment or correction of a spinal condition or deformity. In the illustrated embodiment of FIG. 10, head 234 has a member 252 extending proximally from proximal end 240 of body 232. Member 252 can be provided with a tool engaging recess in its proximal end 246 for engagement with a driving tool used to threadingly insert body portion 232 into the vertebral body. Member 252 has a concave arc shape between proximal end 240 of body 232 and a lip 254 extending around and outwardly from member 252, providing a platform for connection of a construct to anchor 230.

Figure 11:
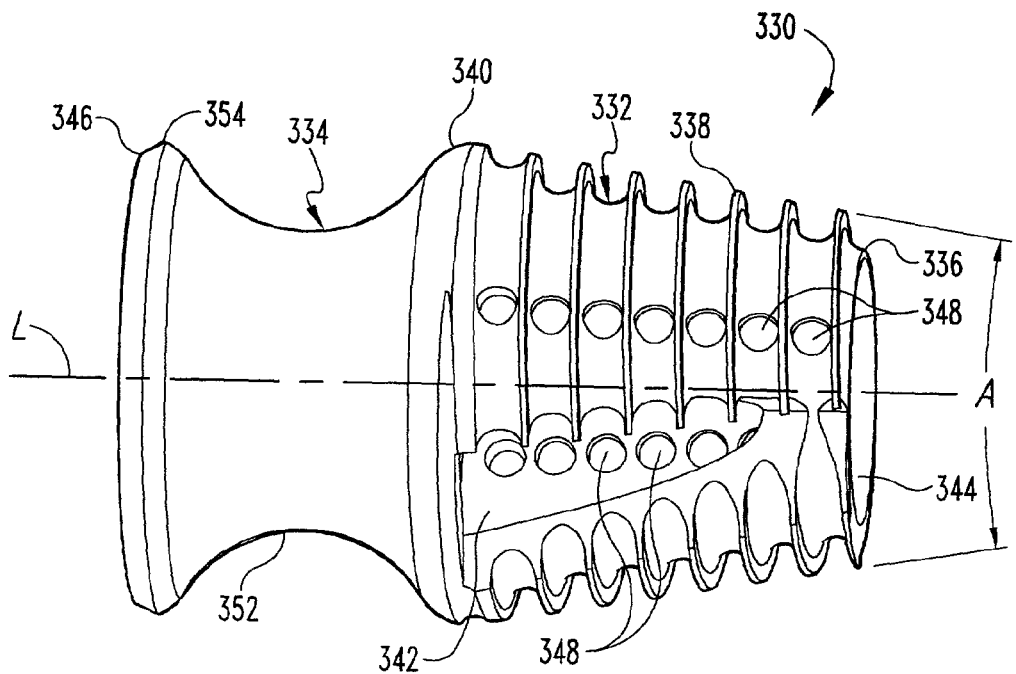
FIG. 11 is an elevational view of a further embodiment bone anchor of the present invention.

In FIG. 11 anchor 330 includes a body 332 and a head 334 extending proximally from a proximal end 340 of body 332. Body 332 extends along a central longitudinal axis L distally from proximal end 340 to a distal insertion end 336. A thread form 338 is formed along body 332 from distal end 336 to proximal end 340 where thread form 338 runs out. Body 332 has a frusto-conical configuration that tapers from a maximum size at proximal end 340 to a minimum size at distal end 336. In one specific embodiment, this taper forms an angle A of about 20 degrees.

Body 332 further includes an opening 342 formed therethrough and in communication with an internal chamber 344. Chamber 344 extends through anchor 330 and opens at the proximal end 346 of head 334 and also opens at the distal end 336 of body 332. Opening 342 has a triangular shape that interrupts thread form 338 and provides an avenue for deposit of bony tissue into the internal chamber as it is severed by thread form 338 during threaded insertion of anchor 330 into bony tissue. The tapered shape of body 332 allows thread form 338 to at least partially engage undisturbed bone as it is inserted, and also allows body 332 to be embedded into the vertebral body in at least partial engagement with undisturbed bone. This enhances the pullout resistance capability of thread form 338.

In the illustrated embodiment, opening 342 extends along a substantial portion of thread form 338 maximizing its opening area for deposit of severed bony tissue. A leading edge of opening 342 can be undercut to facilitate bone harvesting and collection. A number of apertures 348 are provided between the crests of thread form 338 on opposite sides of body 332. Apertures 348 provide additional avenues for bone growth for fusion of anchor 330 to the vertebral body.

Head 334 extends from the vertebral body when body 332 is embedded in the vertebral body. As described further below, head 334 can be provided with any configuration for attachment of a construct thereto for treatment or correction of a spinal condition or deformity. In the illustrated embodiment of FIG. 11, head 334 has a member 352 extending proximally from proximal end 340 of body 332. Member 352 can be provided with a tool engaging recess in its proximal end 346 for engagement with a driving tool used to threadingly insert body portion 332 into the vertebral body. Member 352 has a concave arc shape between proximal end 340 of body 332 and a lip 354 extending around and outwardly from member 352, providing a platform for connection of a construct to anchor 330.

Figure 12:
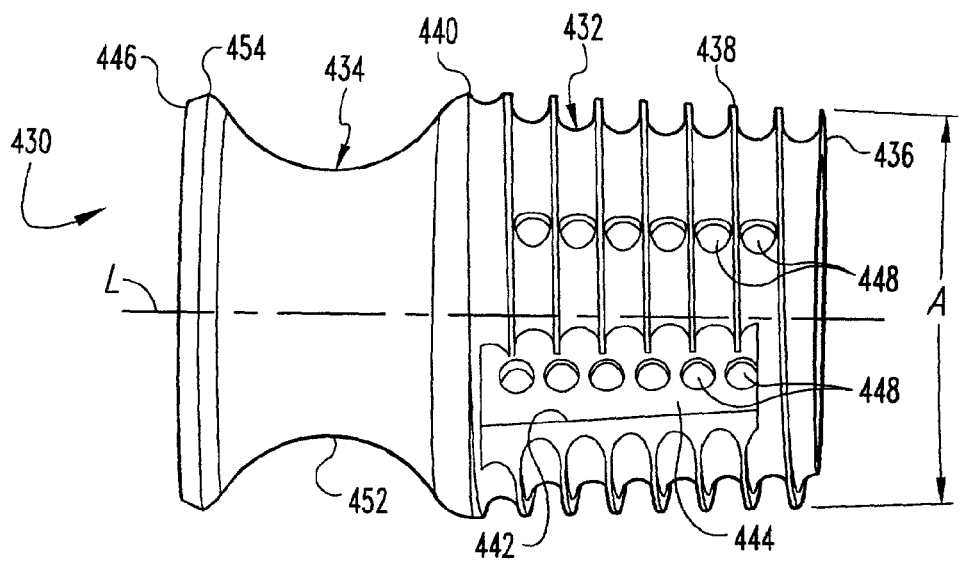
FIG. 12 is an elevational view of another embodiment bone anchor of the present invention.

In FIG. 12 anchor 430 includes a body 432 and a head 434 extending proximally from a proximal end 440 of body 432. Body 432 extends along a central longitudinal axis L distally from proximal end 440 to a distal insertion end 436. A thread form 438 is formed along body 432 from distal end 436 to proximal end 440 where thread form 438 runs out. Body 432 has a frusto-conical configuration that tapers from a maximum size at proximal end 440 to a minimum size at distal end 436. In one specific embodiment, this taper forms an angle A of about 10 degrees.

Body 432 further includes an opening 442 formed therethrough and in communication with an internal chamber 444. Chamber 444 extends through anchor 430 and opens at the proximal end 446 of head 434 and also opens at the distal end 436 of body 432. Opening 442 has a rectangular shape and interrupts thread form 438 and provides an avenue for deposit of bony tissue into the internal chamber as it is severed by thread form 438 during threaded insertion of anchor 430 into bony tissue. The tapered shape of body 432 allows thread form 438 to at least partially engage undisturbed bone as it is inserted, and also allows body 432 to be embedded into the vertebral body in at least partial engagement with undisturbed bone. This enhances the pullout resistance capability of thread form 438.

In the illustrated embodiment, opening 442 extends along a substantial portion of thread form 438 to maximize its opening area for deposit of severed bony tissue. The leading edge of opening 442 can be undercut to facilitate bone harvesting and collection. A number of apertures 448 are provided between the crests of thread form 438 on opposite sides of body 432. Apertures 448 provide an additional avenue for bone growth for fusion of anchor 430 to the vertebral body.

Head 434 extends from the vertebral body when body 432 is embedded in the vertebral body. As described further below, head 434 can be provided with any configuration for attachment of a construct thereto for treatment or correction of a spinal condition or deformity. In the illustrated embodiment of FIG. 12, head 434 has a member 452 extending proximally from proximal end 440 of body 432. Member 452 can be provided with a tool engaging recess in its proximal end 446 for engagement with a driving tool used to threadingly insert body portion 432 into the vertebral body. Member 452 has a concave arc shape between proximal end 440 of body 432 and a lip 454 extending around and outwardly from member 452, providing a platform for connection of a construct to anchor 430.

Figure 13A:
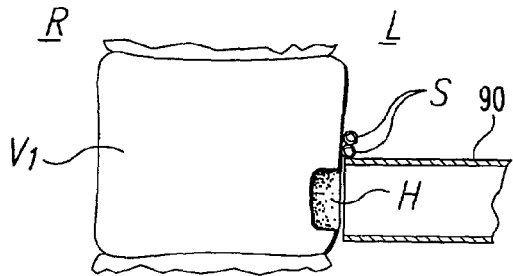
FIGS. 13a and 13b are anterior and lateral views, respectively, of a first step of one method for engaging the bone anchor to a vertebral body.
Figure 13B:
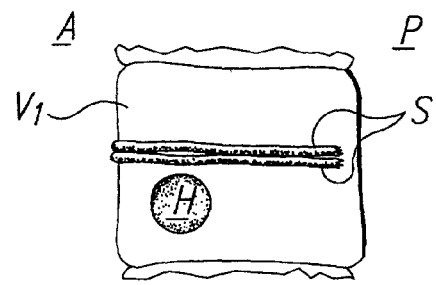

One example of an endoscopic approach for engaging an anchor to a vertebral body will be described with reference to FIGS. 13a-13b and 14a-14b. In FIGS. 13a-13b, vertebral body V1 has been accessed via an endoscopic approach below segmental vessels S. Access tube 90 is placed at the desired location relative to vertebra V1, and a small starting hole H is formed through tube 90. Hole H extends through the cortical bone of vertebra V1 with minimal removal of cancellous bone. In the figures, hole H is formed in left side L of vertebra V1. However, it is also contemplated access tube 90 could be located so that hole H could be formed on right side R, anterior side A, posterior side P, or any other desired location on vertebra V1. It is also contemplated that hole H could be formed with an open surgical technique for accessing vertebrae V1.

Figure 14A:
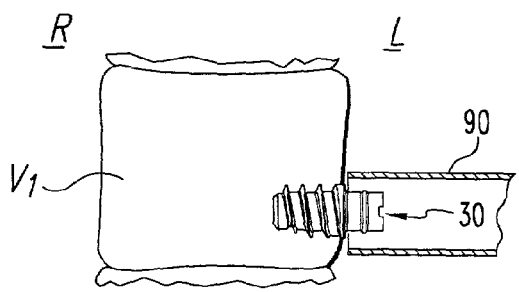
FIGS. 14a and 14b are anterior and lateral views, respectively, of a second step of the one method for engaging the bone anchor to a vertebral body.
Figure 14B:
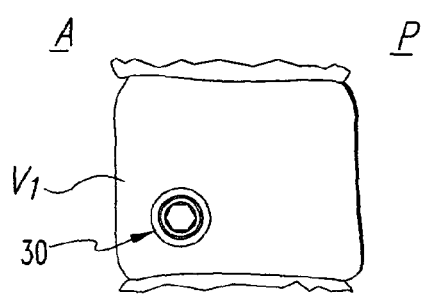

Hole H is sized such that it is slightly larger than the distal end of anchor 30. In FIGS. 14a-14b, an anchor, such as anchor 30, is threadingly inserted into the vertebra V1 into hole H through access tube 90. It is contemplated that anchor 30 and thread form 38 can be self-drilling and self-tapping such that hole need not be drilled or tapped for insertion of anchor 30. It is further contemplated that guidewires are not required for insertion of anchor 30, and that insertion can be monitored with a minimal requirements for fluoroscopy. Cortical bone at opening H and cancellous bone in vertebra V1 are harvested by the threads of anchor 30 and deposited into its chamber during insertion. Additional graft material or bone growth material can be placed into the chamber of anchor 30 to completely fill chamber 30. Access tube 90 can be repositioned relative to vertebra V1 or over a second vertebra for insertion of one or more additional anchors 30.

Constructs can be used to treat a spinal deformity or condition by engaging at least one construct to one or more anchors engaged to one or more vertebrae. A wide variety of surgical approaches and techniques for accessing the spinal column may be used in securing anchors to vertebral bodies and connecting the constructs to the anchors. Such techniques include open surgical techniques in which skin and tissue are retracted to expose the spinal column and minimally invasive endoscopic techniques, including microsurgery. The surgical approach may also be any one or combination of anterior, lateral, posterior, postero-lateral, or antero-lateral approaches employing either open, endoscopic, or microscopic procedures and combinations thereof. It is further contemplated that constructs could be secured to any portion of the spinal column, including the cervical, thoracic, lumbar and sacral regions.

The anchors described herein can be used for the correction or treatment of a spinal deformity or condition through attachment of a stabilization construct to one or more vertebrae along the affected segment of the spinal column. It is contemplated that the anchors can be attached to tethering constructs, plate constructs and/or rod constructs to one or more vertebrae. Examples of such constructs include, but are not limited to, staples, cables, artificial strands, rods, plates, springs, artificial ligaments, and combinations thereof. Such constructs can be rigid, semi-rigid, flexible, partially flexible, resorbable, non-resorbable, superelastic, or include shape-memory material. Further examples of tether constructs include those that are single strand, multiple strands, braided, or combinations thereof. Tether material can include but is not limited to polymers, such as polyester and polyethylene; superelastic metals, such as nitinol; shape memory alloy, such as nickel titanium; resorbable synthetic materials, such as suture material, metals, such as stainless steel and titanium; synthetic materials, allograft material; and bioelastomer material.

Once the one or more anchors are in place, one or more plate, rod or tethering constructs can be connected to the anchors using constrained, unconstrained, semi-constrained connections or combinations thereof. For example, the connection could be unconstrained so that the construct could be allowed to slide relative to the anchor. An example of a semi-constrained connection is a ball joint that allows at least some range of articulation of the construct relative to the anchor, or float within a neutral zone. Examples of constrained or semi-constrained connections include a construct that is wrapped around, crimped, clamped or penetrated by a portion of the anchor or a set screw or cap engageable to the anchor. Such constrained connections fix the construct to the anchor so that there is no or minimal relative movement therebetween. It is further contemplated that the construct can have either a fixed length between anchors or a variable length, or combinations of fixed and variable lengths between anchors. Such fixed and/or variable length constructs can be provided with any combination of constrained, semi-constrained, or unconstrained connections with each anchor.

One specific application of the present invention will now be described with respect to fusionless treatment of scoliosis. Such treatment is provided by attaching a tethering construct to anchors engaged to the vertebral bodies on the convex side of the spine. The tethering construct can correct, arrest or at least minimize growth on the convex or "long" side of the spine, thereby allowing the concave or "short" side of the spine to grow and catch up with the long side. Alternatively, fusionless tethering may treat abnormal spinal alignment by simply preventing further misalignment such as curve progression.

Figures 15A, 15B:
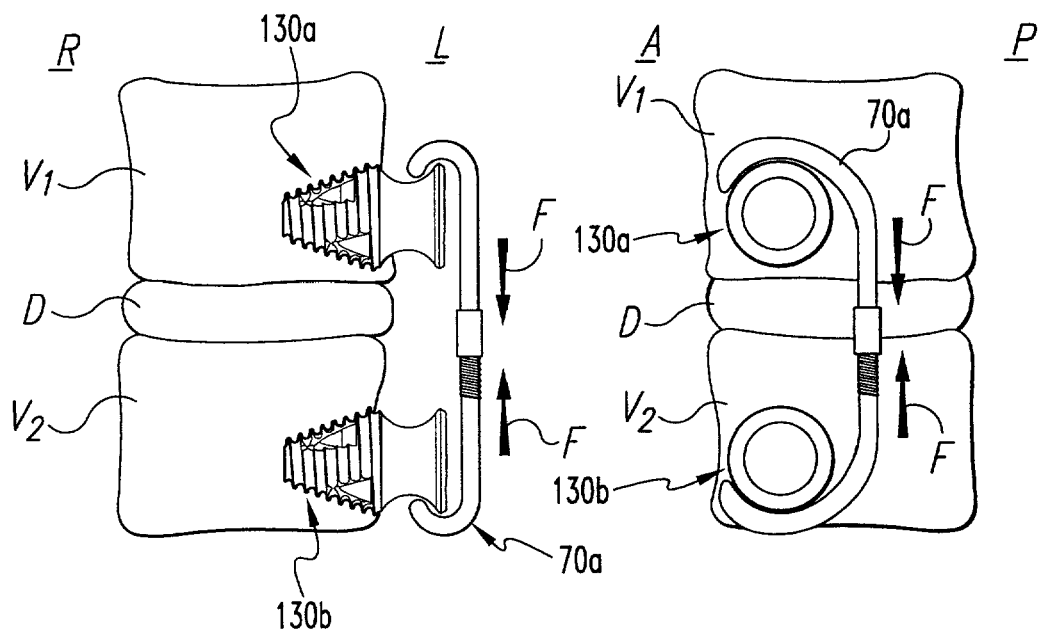
FIGS. 15a and 15b are anterior and lateral views, respectively, illustrating the application of a compressive load to first and second bone anchors engaged to first and second vertebral bodies, respectively.
Figure 16:
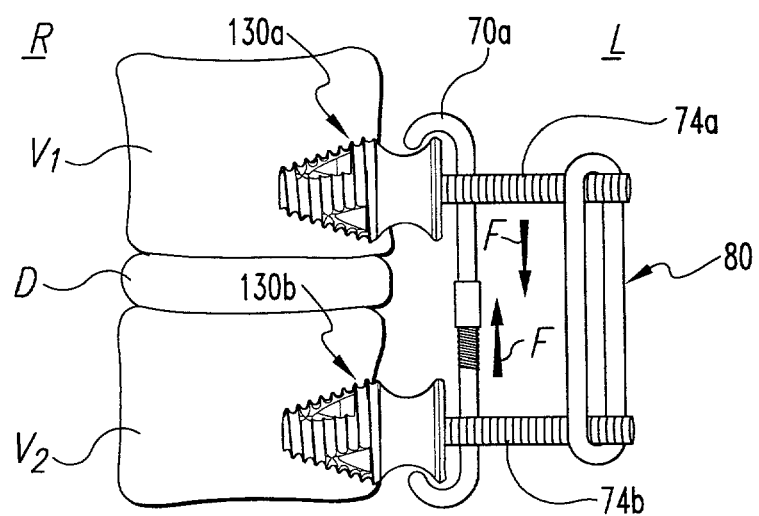
FIG. 16 is an anterior view illustrating the loading of a tether onto anchor extensions engaged to the first and second bone anchors of FIGS. 15a and 15b while compressive force is maintained on the first and second bone anchors.

In FIGS. 15a-15b, anchors, such as anchors 130a and 130b described above, have been engaged to vertebrae V1 and V2, respectively, of a spinal column segment having scoliatic curvature. It is contemplated that any of the anchor embodiments described herein could be engaged to vertebrae V1 and V2. It is further contemplated that the installation of anchors and tethers can be performed either endoscopically or non-endoscopically. A compression device 70a is coupled to the heads of anchors 130a, 130b, and a compressive force is applied to the anchors as indicated by arrows F to obtain the desired corrective forces. The end opening in the heads of anchors 130a, 130b remain accessible for insertion of loading members or anchor extensions 74a, 74b as shown in FIG. 16. In the illustrated embodiment, anchor extensions 74a, 74b are elongated rods that can be securely positioned in the anchors and extend proximally therefrom.

Figure 17:
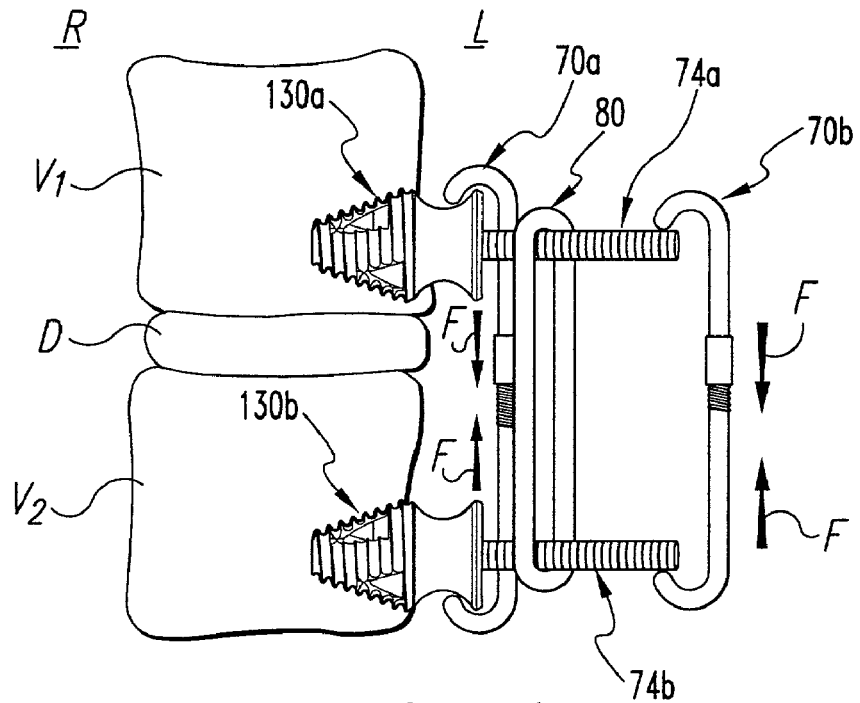
FIG. 17 is an anterior view illustrating the advancement of the tether along the anchor extensions and the application of a compressive force through anchor extensions in combination with the application of the compressive force to the anchors.

A tethering construct in the form a flexible loop tether 80 can be placed around the proximal ends of anchor extensions 74a, 74b while compression is maintained with compression device 70a. Other types of tethering constructs are also contemplated, such as, for example, tethers that are looped at opposite ends. Tether 80 is then advanced distally along anchor extensions 74a, 74b until it is adjacent compression device 70a as shown in FIG. 17. Before or after this advancement, a second compression device 70b is coupled to the proximal ends of anchor extensions 74a, 74b. The desired corrective compressive force is applied to anchors 130a, 130b through anchor extensions 74a, 74b with second compression device 70b.

Figure 18:
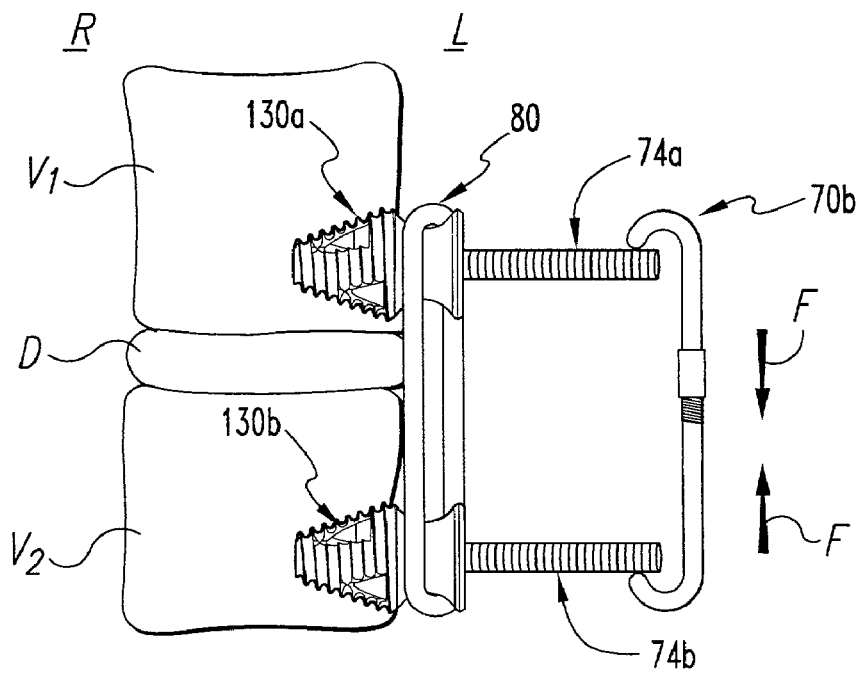
FIG. 18 is an anterior view illustrating the engagement of the tether to the anchors while the compressive force on the anchors is maintained through the anchor extensions.

As shown in FIG. 18, first compression device 70a can then be removed. Tether 80 is advanced distally off of anchor extensions 74a, 74b and onto the platforms of the heads of anchors 130a, 130b. The attachment locations for tether 80 on the heads of the anchors 130a, 130b are spaced farther apart than anchor extensions 74a, 74b, causing tether 80 to further stretch and apply the desired compressive force to anchors 130a, 130b when loaded thereon. Second compression device 70b and anchor extensions 74a, 74 can then be removed, and tether 80 maintains anchors 130a, 130b in compression, as shown in FIG. 19.

The grooved platform of anchor 130 can be larger than the cross-sectional dimension of tether 80 such that it can hold tether 80 on anchor 130 without cap to prevent dislodgement. It is also contemplated that the grooved platform can be large enough to accommodate a pair of tethers 80 to link more than two anchors to a middle anchor. Additional bone graft can be placed into the chamber of anchors 130a, 130b through the proximal end opening. A cap, such as cap 60 described above, or a plug 84 can be engaged to anchors 130a, 130b and extend into the chamber to compress the graft material and harvested bone in the anchors.

The use of a flexible tether 80 preserves multiple planes of motion of the vertebrae without compromising the stabilization effect. Further, flexible tether 80 can slide with respect to the head of the anchor without compromising the stabilization effect between motion segments. A flexible tether 80 also produces less deleterious effects on spinal disc D since some range of segmental motion is preserved. The non-rigid attachment of the tether to the anchor protects the anchor since less forces are delivered to the anchor than would be delivered with a rigid attachment. The tether is also protected from high stresses at the point of attachment since the forces are distributed over the head of the anchor rather than concentrated at a fixed point on the tether. The flexible tether can also assume gradual changes in direction of the tether while minimizing stress points on the tether and the anchor, and minimizing friction and wear between the tether and the anchor.

Referring now to FIGS. 20a and 20b, crimps can be placed around tether 80 to supply additional compressive forces between anchors 130a, 130b. In the illustrated embodiment, there is a first crimp 86a adjacent anchor 130a, a second crimp 86b adjacent anchor 130b, and a third crimp 86c between first crimp 86a and second crimp 86b. Crimps 86 tighten tether 80 by moving the first and second portions of the tether extending along the vertebrae toward one another, thereby increasing its tension to supply additional corrective compressive force to anchors 130a, 130b. It is contemplated that less than three crimps or more than three crimps could be used depending on the desired corrective force to be applied to anchors 130a, 130b.

Crimps 86 can be in the form a loop that is pre-positioned around the middle of tether 80 before it is loaded onto anchors 130a, 130b, and then moved along the loaded tether 80 towards the anchors to supply additional compressive forces. Crimps 86 can also be provided in an un-looped form, and wrapped around the loaded tether 80 and secured in looped form to supply the desired compressive forces. Crimps 86 can be placed endoscopically along with tether 80 or through an open procedure.

Crimps 86 that are in the form of loops can have a circular, oval, rectangular, or any other shape that will extend around tether 80. Crimps 86 can be made from flexible or semi-rigid material that will maintain its position with respect to tether 80 when placed therearound unless forcibly moved or removed. The diameter of the crimp and its width W along tether 80 can be selected to provide the desired amount of tension to tether 80 when crimp 86 is placed therearound. Crimps 86 also tighten the tether around the head of the anchor to reduce the risk of dislodgement of the tether.

Referring now to FIGS. 21a-21b, a system of anchors 130a, 130b, 130c, 130d, 130e, 130f are engaged to vertebrae V1, V2, V3 as shown. Tethering is provided across each of the spinal discs D between adjacent vertebrae. For example, tether 80a is connected to anchors 130b and 130c of vertebrae V1 and V2, respectively. Tether 80b is connected to anchors 130d and 130e of vertebrae V2 and V3, respectively. Tethering is not provided between anchors engaged to the same vertebral body. This allows the segmental vessel S to be preserved while the desired corrective compressive forces are applied across the motion segments of the vertebrae. It is also contemplated that segmental vessels S can be ligated and tethers extend between each pair of adjacent anchors. It is further contemplated that only a single anchor can be engaged to each vertebral body, and that each anchor is tethered to anchors of the adjacent vertebral bodies.

Referring now to FIGS. 22a-22c, there is shown a loading instrument 90 for loading a tether onto an anchor engaged to a vertebra. Loading instrument 90 includes an inner shaft 92 (FIG. 22a) and an outer shaft 94 (FIG. 22b.) Outer shaft 94 is slidably mounted on inner shaft 92 (FIG. 22c), and outer shaft 94 is movable along inner shaft 92 by actuating a handle (not shown) connected at the proximal ends of the inner and outer shafts. It is contemplated that the handle can be a Kerrison-type handle or other suitable device for moving outer shaft 94 relative to inner shaft 92.

Inner shaft 92 has a distal end 98 that includes a scalloped surface 100 and a tether staging surface 102 opposite scalloped surface 100. Inner shaft 92 has a distal protrusion 96 extending distally therefrom that is positionable into the proximal end opening of the anchor. Outer shaft 94 has a tether engaging member 104 at its distal end that is positioned around distal end 98 of inner shaft 92 adjacent tether staging surface 102.

Figure 23:
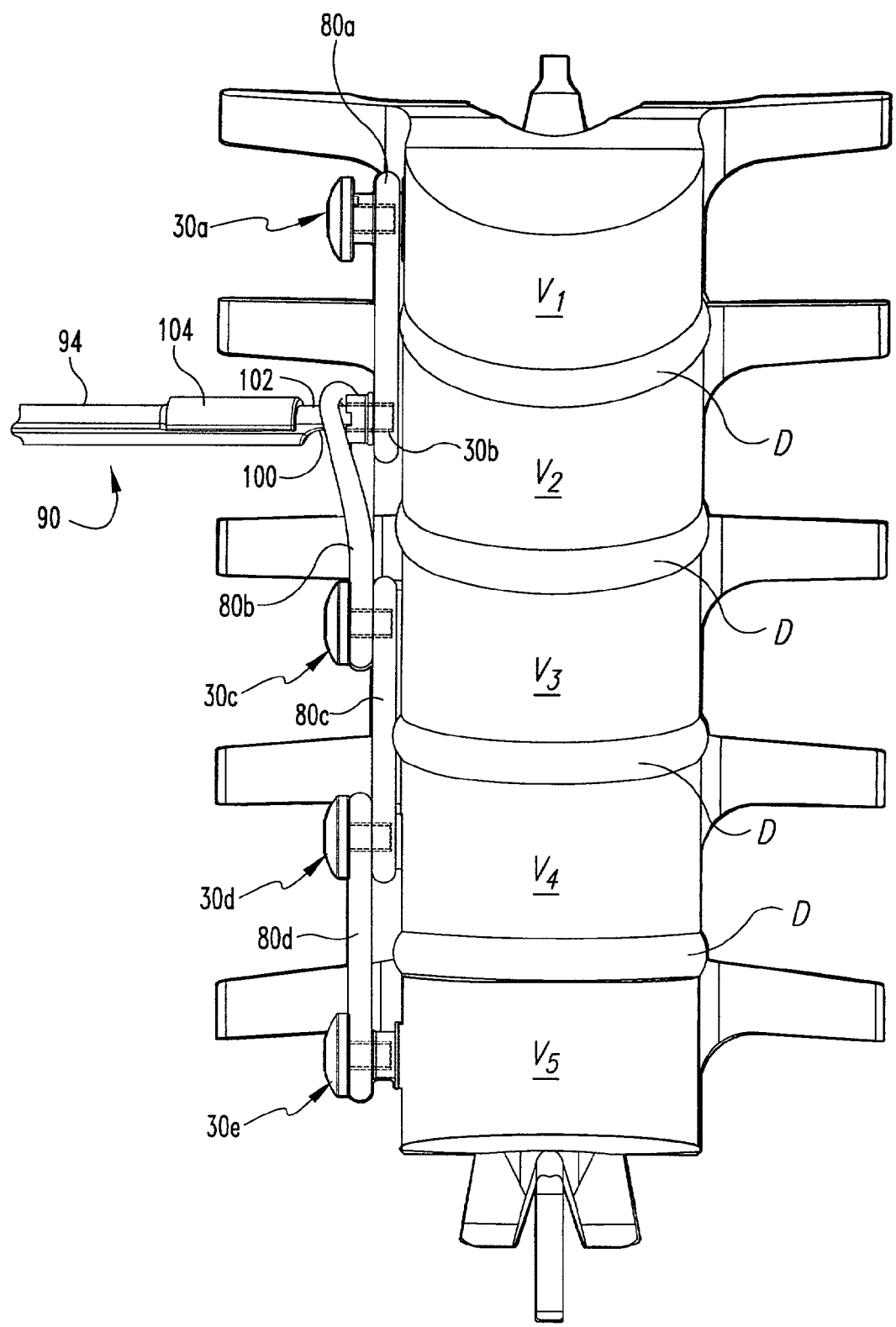
FIG. 23 is an anterior view showing one embodiment of a system of interconnecting five vertebral bodies with bone anchors and tethers along with use of the tether loading instrument of FIGS. 22a-22c to load a tether on an anchor.

Referring now further to FIG. 23, one example of a method for positioning a tether on an anchor with loading instrument 90 will be described. Tether 80b is placed around anchor 30c, and the distal end of inner shaft 92 is placed through the upper end of tether 80b with scalloped surface 100 oriented upwardly (opposite that shown in FIG. 23.) Protrusion 96 is positioned in the proximal end opening of anchor 30b. Loading instrument 90 is rotated 180 degrees about its longitudinal axis with protrusion 96 in anchor 30b so that tether 80b is positioned on tether staging surface 102. Tether staging surface 102 is generally aligned with the upper surface of the platform defined by the head of anchor 30b. Outer shaft 94 is then moved distally in the direction of arrow T with respect to inner shaft 92 so that the distal end of tether engaging member 104 contacts tether 80b and pushes it distally along inner shaft 92 and onto the head of anchor 30b.

Figure 24B:
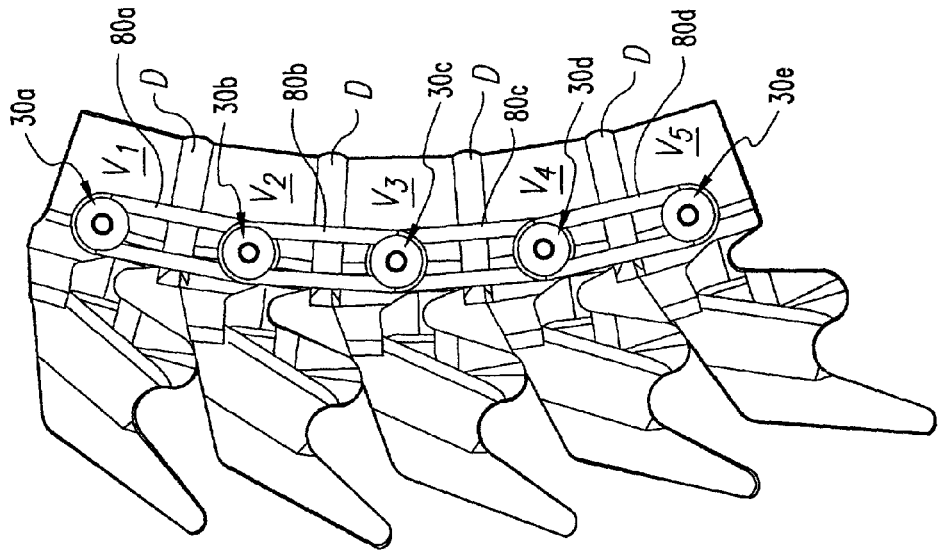
FIGS. 24a and 24b are antero-lateral and lateral views, respectively, showing another embodiment of a system of interconnecting a segment of vertebral bodies with bones anchors and tethers.
Figure 24A:
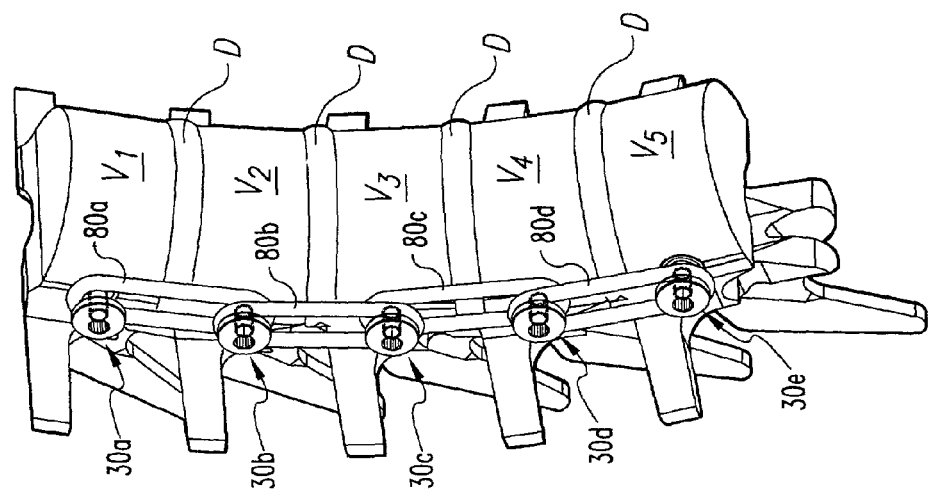

Referring now to FIGS. 24a-24b, one example of a tethering system employing looped tethers 80 and anchors 30 to correct scoliosis of the spinal column is provided. In this embodiment, anchors 30a, 30b, 30c, 30d, 30e are engaged to vertebrae V1, V2, V3, V4, V5, respectively. Tether 80a is engaged to the distal platforms of anchors 30a, 30b and tether 80c is engaged to the distal platforms of anchors 30c, 30d. Tether 80b is engaged to the proximal platforms of anchors 30b, 30c and tether 80d is engaged to the proximal platforms of anchors 30d, 30e. Caps 60 are engaged to respective ones of the anchors to compress and maintain the graft material in the anchors and to secure the tethers on the anchors.

Figure 25A:
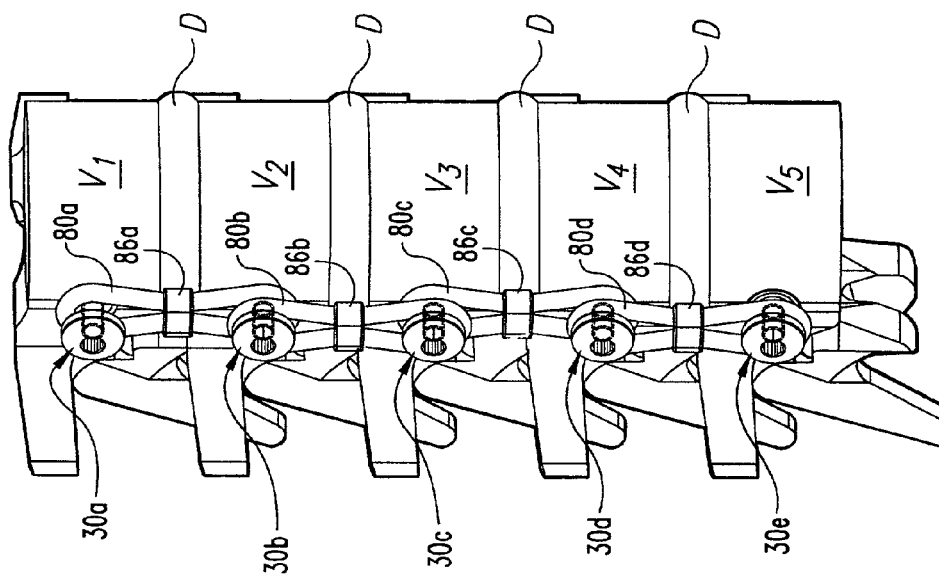
FIGS. 25a and 25b are antero-lateral and lateral views, respectively, showing yet another embodiment of a system of interconnecting a segment of vertebral bodies with bones anchors, tethers and crimps.
Figure 25B:
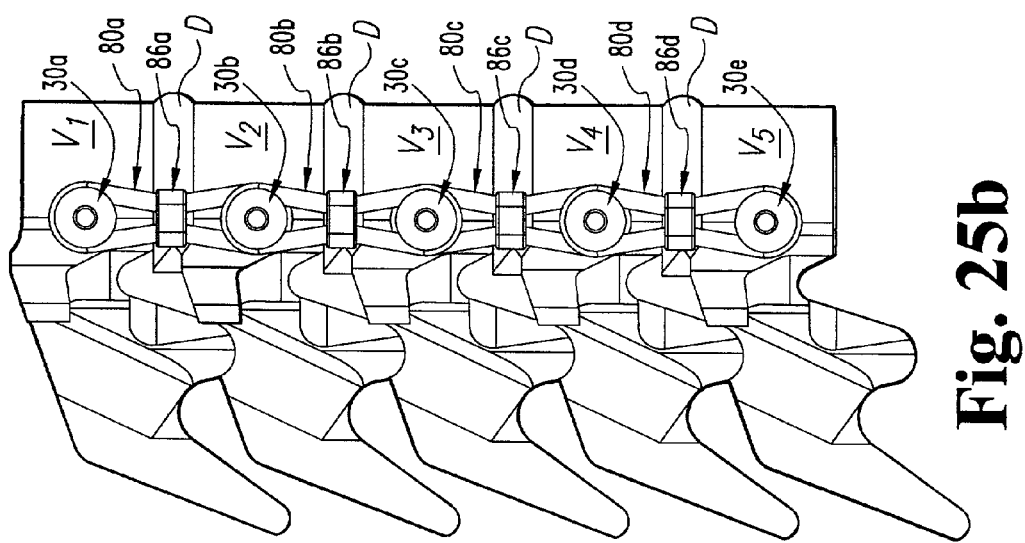

Referring now to FIGS. 25a-25b, there is shown the system of FIGS. 24a-24b with crimped tethers. Crimp 86a is placed around tether 80a, crimp 86b is placed around tether 80b, crimp 86c is placed around tether 80c, and crimp 86d is placed around tether 80d. It is contemplated that additional crimps can be placed around the tethers as desired to increase the corrective compressive force on the anchors. It is also contemplated that crimps 86 can be pre-loaded on tethers 80 before attachment to anchors 80 or configured to be attached to tethers 80 after tethers 80 are engaged to the anchors.

While the invention has been illustrated and described in detail in the drawings and foregoing description, the same is to be considered illustrative and not restrictive in character, it being understood that only the preferred embodiments have been shown and described and that all changes and modifications that come within the spirit of the invention are desired to be protected.

What is claimed is:
1. A bone anchor, comprising:
a body engageable intravertebrally to a vertebra, said body having a proximal end, a distal end, and a thread form extending along at least a portion of said body, said body further defining a chamber opening at said distal end and said body having a tapered profile from said proximal end to said distal end to form a frusto-conical shape between said proximal end and said distal end wherein said thread form runs out at said proximal end and said thread form at said proximal end is at least partially engageable with undisturbed bone of the vertebra; and a head extending from said proximal end of said body and positioned outside the vertebra when said body is engaged to the vertebra.

2. The bone anchor of claim 1, wherein said body has a minimum size at said distal end and a maximum size at said proximal end.

3. The bone anchor of claim 1, wherein said distal end of said body is beveled to facilitate insertion of said body into the vertebra.

4. The bone anchor of claim 1, wherein said thread form extends between said proximal end and said distal end of said body.

5. The bone anchor of claim 2, wherein said entire thread form is engageable to undisturbed bone along said body.

6. The bone anchor of claim 2, wherein said thread form has a self-tapping configuration.

7. The bone anchor of claim 1, wherein said frusto-conical, tapered body forms a taper angle.

8. The bone anchor of claim 7, wherein said taper angle is the range from 5 degrees to 45 degrees.

9. The bone anchor of claim 7, wherein said taper angle is about 5 degrees.

10. The bone anchor of claim 1, wherein said head includes a recessed surface defining an exterior surface of said head, said recessed surface extending completely about said head between said proximal end of said body and a proximal end of said head.

11. The bone anchor of claim 10, wherein said head further includes a lip extending around said exterior surface of said head and outwardly from said recessed surface separating said recessed surface into a proximal platform and a distal platform.

12. The bone anchor of claim 10, wherein said recessed surface has a concave profile extending between said proximal end of said body and said proximal end of said head.

13. The bone anchor of claim 1, wherein said head has a proximal end and said chamber extends through said head and opens at said proximal end of said head.

14. The bone anchor of claim 13, wherein said chamber defines a tool engaging portion adjacent said proximal end of said head.

15. The bone anchor of claim 13, further comprising a cap engageable to said head such that said cap is located proximally of said head.

16. The bone anchor of claim 15, wherein said cap includes an end member extending radially about said proximal end of said head.

17. The bone anchor of claim 15, wherein said cap includes a stem engageable to said head in said chamber.

18. The bone anchor of claim 17, wherein said stem compresses bone material in said chamber when said cap is engaged to said head.

19. The bone anchor of claim 1, wherein said thread form is interrupted by a number of openings extending through said body and in communication with said chamber, wherein bone material cut by said thread form as said body is threadingly engaged to the vertebra is deposited through said openings into said chamber, whereby bone growth occurs through said body to fuse said body with the vertebra.

20. The bone anchor of claim 19, wherein said number of openings is in the range from one to three openings.

21. The bone anchor of claim 19, wherein each of said number of openings has an oval shape centered on and extending along said thread form.

22. The bone anchor of claim 19, wherein said number of openings are staggered about said body.

23. The bone anchor of claim 19, wherein said number of openings are spaced along said thread form such that when a first one of said number of openings is positioned at a first depth in the vertebra at least one complete revolution of said body along said thread form is required before a second one of said number of openings is positioned at said first depth in the vertebra.

24. The bone anchor of claim 19, wherein each of said number of openings has a triangular shape with an apex of said shape oriented toward said distal end of said body.

25. The bone anchor of claim 19, wherein each of said number of openings has a rectangular shape.

26. A bone anchor, comprising:
a head; and
a body extending distally from said head, said body engageable intravertebrally to a vertebra by a thread form extending at least partially along said body, said body having a proximal end, a distal end, and a tapered profile extending therebetween forming a frusto-conical shape between said distal end and said proximal end, said body defining a chamber and a number of openings interrupting said thread form in communication with said chamber, wherein said chamber opens at said distal end, and bone material cut by said thread form as said body is threadingly engaged to the vertebra is deposited through said openings into said chamber whereby fusion of the bone anchor to the vertebra occurs through said chamber.

27. The bone anchor of claim 26, wherein said number of openings is in the range from one to three openings.

28. The bone anchor of claim 26, wherein each of said number of openings has an oval shape centered on and extending along said thread form.

29. The bone anchor of claim 26, wherein said number of openings are staggered about said body.

30. The bone anchor of claim 26, wherein said number of openings are spaced along said thread form such that when a first one of said number of openings is positioned at a first depth in the vertebra at least one complete revolution of said body along said thread form is required before a second one of said number of openings is positioned at said first depth in the vertebra.

31. The bone anchor of claim 26, wherein each of said number of openings has a triangular shape with an apex of said shape oriented toward said distal end of said body.

32. The bone anchor of claim 26, wherein each of said number of openings has a rectangular shape.

33. The bone anchor of claim 26, wherein said frusto-conical, tapered body forms a taper angle in the range from about 5 degrees to about 45 degrees.

34. The bone anchor of claim 26, wherein said chamber is tapered from said proximal end of said body toward said distal end of said body.

35. The bone anchor of claim 26, further comprising a cap having a stem engageable to said head in said chamber, wherein said stem compresses bone material in said chamber.

36. The bone anchor of claim 35, further comprising graft material in said chamber, wherein said graft material is compressed by said stem.

37. The bone anchor of claim 26, wherein:
said chamber receives bone material from the vertebra therethrough as said body is threadingly engaged to the vertebra.

38. The bone anchor of claim 37, wherein the bone material deposited through said number of openings provides bony continuity between bone material received through said distal end opening of said chamber and bone material of the vertebra around said body.

39. The bone anchor of claim 38, wherein said tapered profile is configured so that said thread form is at least partially engageable with undisturbed bone to secure the bone anchor in the vertebra.

40. The bone anchor of claim 26, wherein said thread form extends between said proximal end and said distal end of said body.

41. The bone anchor of claim 40, wherein said thread form is entirely engageable to undisturbed bone along said body.

42. The bone anchor of claim 40, wherein said thread form has a self-tapping configuration.

43. A bone anchor, comprising:
   a head; and
   a body extending distally from said head, said body extending between a proximal end adjacent said head and a distal end, said body including:
      a thread form configured for at least partial engagement with undisturbed bone of a vertebra to which said body is intravertebrally engaged;
      a chamber opening at said distal end;
      at least one opening interrupting said thread form in communication with said chamber, wherein:
         bone material cut by said thread form as said body is threadingly engaged to the vertebra is deposited through said at least one opening into said chamber,
         bone material from the vertebra is received into said chamber through said distal end opening as said body is threadingly engaged to the vertebra; and
         the bone material deposited through said number of openings provides bony continuity between bone material received through said distal end opening of said chamber and bone material of the vertebra around said body for fusion of said body with the vertebra.

44. The bone anchor of claim 43, wherein said chamber extends through said head and opens at a proximal end thereof.

45. The bone anchor of claim 43, wherein the bone material deposited through said number of openings provides continuity between bone material received through said distal end opening of said chamber and bone material of the vertebra around said body.

46. The bone anchor of claim 43, wherein said body has a tapered profile extending from said proximal end to said distal end.

47. The bone anchor of claim 43, wherein said chamber is tapered from said proximal end of said body toward said distal end of said body.

48. A spinal stabilization system, comprising:
   a first bone anchor having a body defining a chamber, said body intravertebrally fuseable with a first vertebra;
   a second bone anchor having a body defining a chamber, said body intravertebrally fuseable to a second vertebra; and
   a stabilization construct extending along the exterior of the first and second vertebrae and connecting said first bone anchor and said second bone anchor
   wherein said stabilization construct is a looped tether and wherein said looped tether includes:
      a first portion extending along a first side of said first and second bone anchors;
      a second portion spaced from said first portion extending along a second side of said first and second bone anchor; and
      at least one crimp extending around said looped tether loop and securing the first and second portions in a position more proximate one another.

49. The system of claim 48, wherein said at least one crimp increases the compressive force applied by said looped tether between said first bone anchor and said second bone anchor.

50. The system of claim 48, wherein said at least one crimp includes a number of crimps spaced along said looped tether between said first and second anchors.

51. A spinal stabilization system, comprising:
   a first bone anchor having a body defining a chamber, said body intravertebrally fuseable with a first vertebra;
   a second bone anchor having a body defining a chamber, said body intravertebrally fuseable to a second vertebra; and
   a stabilization construct extending along the exterior of the first and second vertebrae and connecting said first bone anchor and said second bone anchor
   wherein said stabilization construct is a boned tether and, wherein said looped tether applies a compressive force between said first bone anchor and said second bone anchor.

52. The system of claim 51, wherein:
   said first bone anchor includes a head extending from said body;
   said second bone anchor includes a head extending from said body; and
   said stabilization construct being engaged to said head of said first anchor and said head of said second anchor.

53. The system of claim 52, further comprising:
   a third bone anchor having a body defining a chamber, said body intravertebrally fuseable with a third vertebra, said third bone anchor including a head extending from said body; and
   said stabilization construct being engaged to said head of said third anchor.

54. The system of claim 52, wherein each of said heads of said first and second bone anchors includes a recessed surface to which said stabilization construct is engaged.

55. The system of claim 54, wherein each of said heads of said first and second bone anchors includes a lip extending around said recessed surface, said lip defining a proximal platform and a distal platform on said recessed surface.

56. The system of claim 55, wherein said stabilization construct includes a first looped tether positionable on one of said proximal and distal platforms of said recessed surface and a second looped tether positionable on the other one of said proximal and distal platforms.

57. A spinal stabilization system, comprising:
   a first bone anchor having a body defining a chamber, said body intravertebrally fuseable with a first vertebra;
   a second bone anchor having a body defining a chamber, said body intravertebrally fuseable to a second vertebra; and
   a stabilization construct extending along the exterior of the first and second vertebrae and connecting said first bone anchor and said second bone anchor
   wherein said stabilization construct is a looped tether and wherein at least one of said first and second bone anchors includes:
      a body engageable intravertebrally to a vertebra, said body having a proximal end, a distal end, and a thread form extending along at least a portion of said body, said body further defining a chamber opening at said distal end and said body having a tapered profile from said proximal end to said distal end to form a frusto-conical shape between said proximal end and said distal end; and a head extending proximally from said proximal end of said body and said looped tether extends around said head.

58. The bone anchor of claim 1, wherein said chamber is tapered from said proximal end of said body toward said distal end of said body.

59. A bone anchor, comprising:

a body engageable intravertebrally to a vertebra, said body having a proximal end, a distal end, and a thread form extending along said body and terminating at said proximal end of said body, said body further defining a chamber opening at said distal end and said body and said chamber each having a tapered profile extending from said proximal end to said distal end to form a frusto-conical shape between said proximal end and said distal end, wherein said thread form at said proximal end is at least partially engageable with undisturbed bone of the vertebra; and a head extending proximally from said proximal end of said body.

60. The anchor of claim 59, wherein said head includes an external surface formed by a concave recess extending about said head, said recess being concavely curved between said proximal end of said body and said proximal end of said head.

61. The anchor of claim 59, wherein said body includes a number of openings therethrough in communication with said chamber.

* * * * *